United States Patent

Davis et al.

[11] Patent Number: 4,592,369
[45] Date of Patent: Jun. 3, 1986

[54] METHOD AND APPARATUS FOR USE IN TEMPORAL ANALYSIS OF WAVEFORMS

[75] Inventors: Graham R. Davis, Gillingham, England; Thomas I. H. Brown, Melbourne, Australia

[73] Assignee: National Research Development Corp., London, England

[21] Appl. No.: 511,891

[22] Filed: Jul. 8, 1983

[30] Foreign Application Priority Data

Jul. 12, 1982 [GB] United Kingdom ............... 8220215

[51] Int. Cl.$^4$ ............................................. A61B 5/04
[52] U.S. Cl. ............................... 128/733; 324/77 R
[58] Field of Search ............... 128/733, 703–704, 128/731–732; 324/77 R, 77 A

[56] References Cited

U.S. PATENT DOCUMENTS

| 3,513,834 | 5/1970 | Suzuki et al. | 128/731 |
| 3,554,187 | 1/1971 | Glassner | 128/703 |
| 3,577,983 | 5/1971 | Baessler | 128/703 X |
| 3,707,959 | 1/1973 | Wilton-Davies | 128/703 |
| 3,978,856 | 9/1976 | Michel | 128/703 |
| 4,083,365 | 4/1978 | Yancey | 128/731 |
| 4,213,467 | 7/1980 | Stulen et al. | 128/733 |

OTHER PUBLICATIONS

Stalberg et al., *Single Fibre Emg.*, pp. 42–45.

*Primary Examiner*—Kyle L. Howell
*Assistant Examiner*—Angela D. Sykes
*Attorney, Agent, or Firm*—Cushman, Darby & Cushman

[57] ABSTRACT

In single fibre electromyography it is useful to be able to measure intervals between waveforms (obtained from needle electrodes inserted into muscle fibres) reaching certain levels. A circuit is described, which is of general application, and which allows such intervals to be measured. First and second comparators which have adjustable reference levels receive an incoming waveform and, by means of polarity select circuits, provide outputs only when the reference levels are passed by waveform portions changing in selected respective directions. The time at which the first comparator is satisfied is available from a counter 33 but it is only passed to a computer interface when the second comparator has also been satisfied. Enable circuits prevent an output to the computer unless the comparators are satisfied within selectable time intervals.

10 Claims, 6 Drawing Figures

METHOD AND APPARATUS FOR USE IN TEMPORAL ANALYSIS OF WAVEFORMS

The present invention relates to a method and apparatus for determining when waveforms satisfy predetermined conditions relating, for example, to level and increasing or decreasing value. Such information is useful in analyzing single fibre electromyographic (SFEMG) waveforms.

Single fibre electromyography is concerned with the study of electrical activity in individual nerve and muscle fibres. Signals are recorded using a hypodermic needle containing one or more electrodes. Each electrode can usually monitor electrical activity in two to three muscle fibres, depending on the fibre density. Information is transmitted around the nervous system as a series of voltage waveform spikes, called action potentials. These spikes propagate along nerve and muscle fibres, using a form of rate modulation to convey information. The propagation of action potentials along a muscle fibre stimulates the force generation process, with increasing force being associated with an increasing pulse frequency. Action potentials in muscle fibres are stimulated by nerve fibres, with one nerve fibre "driving" a number of muscle fibres. A group of muscle fibres connected to a single nerve fibre is called a motor unit. Needle electrodes usually pick up action potentials from two or three muscle fibres in the same motor unit. This means that a number of spikes will be seen synchronised with each other but separated in time due to a difference in propagation delay.

The size and shape of action potentials is usually insignificant since all the information is contained in the timing of the spikes or pulses. Thus the study of single fibre electromyography is concerned with the measurement of time intervals only. The two main measurements are the inter-discharge interval (IDI) and the inter-potential interval (IPI). The inter-discharge interval is the time between consecutive action potentials in a single fibre. The inter-potential interval is the time difference between synchronized action potentials in two fibres of the same motor unit. The IDI varies from about 10 ms to 200 ms for most muscles and the IPI varies up to about 3 ms in normal cases and up to 20 to 30 ms in extreme cases of disease. A useful measurement is the variability of the inter-potential interval called the jitter. The jitter can be used as a measure of the extent of neuromuscular disorder in diseased patients, and the way in which jitter changes with changing conditions, fatigue and temperature for example, can be useful in diagnosis. At the moment measurement techniques in this field are limited and so there is a need for instrumentation capable of extracting temporal data from analogue signals.

According to a first aspect of the present invention there is provided apparatus for indicating when a waveform satisfies selected conditions, comprising first and second comparators for comparing the instantaneous value of a waveform with first and second reference values, respectively, means for adjusting the first and second reference values, means for generating a gating signal when the instantaneous value of the waveform has attained both a first predetermined relationship with the first reference value and a second predetermined relationship with the second reference value, clock means for providing an indication of time elapsing, latch means for holding the value of the clock means at the instant the first predetermined relationship is satisfied, and gate means for passing the contents of the latch means to output when the gating signal is generated.

The first and second relationships with the reference values may be the directions in which the waveform crosses reference levels corresponding to the values and the apparatus may include means for selecting the said directions separately for each reference level. For example the first relationship may be satisfied when the waveform crosses the first reference level going positive and the second relationship may be satisfied when the waveform crosses the second reference level going negative.

The time indicated by the clock means is not usually in any specific relationship with conventional geographical time.

An advantage of the apparatus according to the invention is that three types of trigger may be selected for an SFEMG waveform:

First type—By adjusting the first and second reference values to the same level and selecting the same relationship, a simple trigger is obtained in which the clock value is read out by the apparatus at the time the selected reference value and relationship are satisfied.

Second type—The first and second relationships correspond to opposite directions with the positive going relationship having the more positive reference value. In a typical example the first relationship is negative going, the first reference value is set near the zero axis and the second relationship is positive going with the second reference value as large positive. The result is that the clock value at a zero crossing following a positive swing of a predetermined magnitude is output by the apparatus.

Third type—The first and second relationships are in the same direction with second reference value being displaced from the first reference value in that direction. In a typical example the first relationship is negative going, with the first reference value set near the zero axis and the second relationship is negative going with the second reference value large, negative. The result is that the clock value at a zero crossing preceding a swing of a predetermined magnitude is output by the apparatus.

The provision of these three types of trigger is advantageous since it allows an operator to select a type which suits the analysis being carried out and the SFEMG waveforms being analysed.

For use in analysing SFEMG waveforms, the apparatus according to the invention preferably includes respective enabling means for each of the first and second comparators which enable the comparators for selectable predetermined intervals. In this way the selected triggers are given time "windows" and can only be satisfied within these windows. As has been mentioned, SFEMG waveforms contain a series of spikes or pulses separated in time and by using the windows selected pulses or groups of pulses can be made available for analysis.

A computer, for example a special purpose computer based on a microprocessor, may be used to generate digital control signals to select the first and second reference levels and/or predetermined relationships, and/or to control the windows. The computer is also usually programmed to carry out a required analysis of intervals between pulses from the apparatus output.

The apparatus according to the invention may include a micro-program memory for storing a sequence of digital words for controlling at least one of the said levels, relationships and windows and each word may have one field for each quantity controlled, and a program counter for controlling read-out from the microprogram memory to trigger logic means which comprises the means for adjusting the first and second reference values, the means for selecting the said directions and the enabling means, the program counter being arranged to be started when the said gating signal is generated.

One advantage of controlling the trigger logic by use of a microprogram is that the two signal comparison channels can be used to provide different trigger conditions during one series of SFEMG signals.

The apparatus may also include display means for displaying portions of waveform applied to the apparatus, the reference values and the durations of the windows (both in analogue form), a signal-data memory for storing signals representing a waveform applied to the apparatus, one storage location (capable of storing one or more digital signals) being provided for each picture element x-coordinate in the display, and a time-base counter, the signal data memory being arranged to read in signals continuously to storage locations in a cyclic sequence under the control of the time base counter.

The display means may also be used to display the results of analysis of intervals carried out by the computer.

Preferably the program counter is connected to disable the time base counter at a predetermined program count such that the signal-data memory then holds signals corresponding to waveform values prior to, and subsequent to, the trigger conditions being satisfied.

Preferably, the micro program memory holds one word corresponding to each respective picture element x-coordinate in the display.

The display means may include a display memory with one location or group of locations for every picture element (pixel) of a raster scan display, an erase memory for storing signals passed from the signal data memory to the display memory, graphics display means for controlling the CRT display and the display memory and a multiplexer for loading the display memory from any of the signal data memory, the erase memory or the graphics display means.

Using a display memory in this way is advantageous since it can be made to operate sufficiently fast to allow a raster scan display circuit to provide a flicker free trace on a television monitor.

According to a second aspect of the present invention there is provided a method providing an indication when a waveform satisfies selected conditions, comprising the steps of setting first and second reference values, comparing the instantaneous value of a waveform with the first and second reference values respectively, generating a gating signal when the instantaneous value of the waveform has attained both a first predetermined relationship with the first reference value and a second predetermined relationship with the second reference value, storing a value representing elapsed time at the instant the first predetermined relationship is satisfied, and passing the stored time value to output when the gating signal is generated.

Certain embodiments of the invention will now be described, by way of example, with reference to the accompanying drawings, in which.

Figure 1:
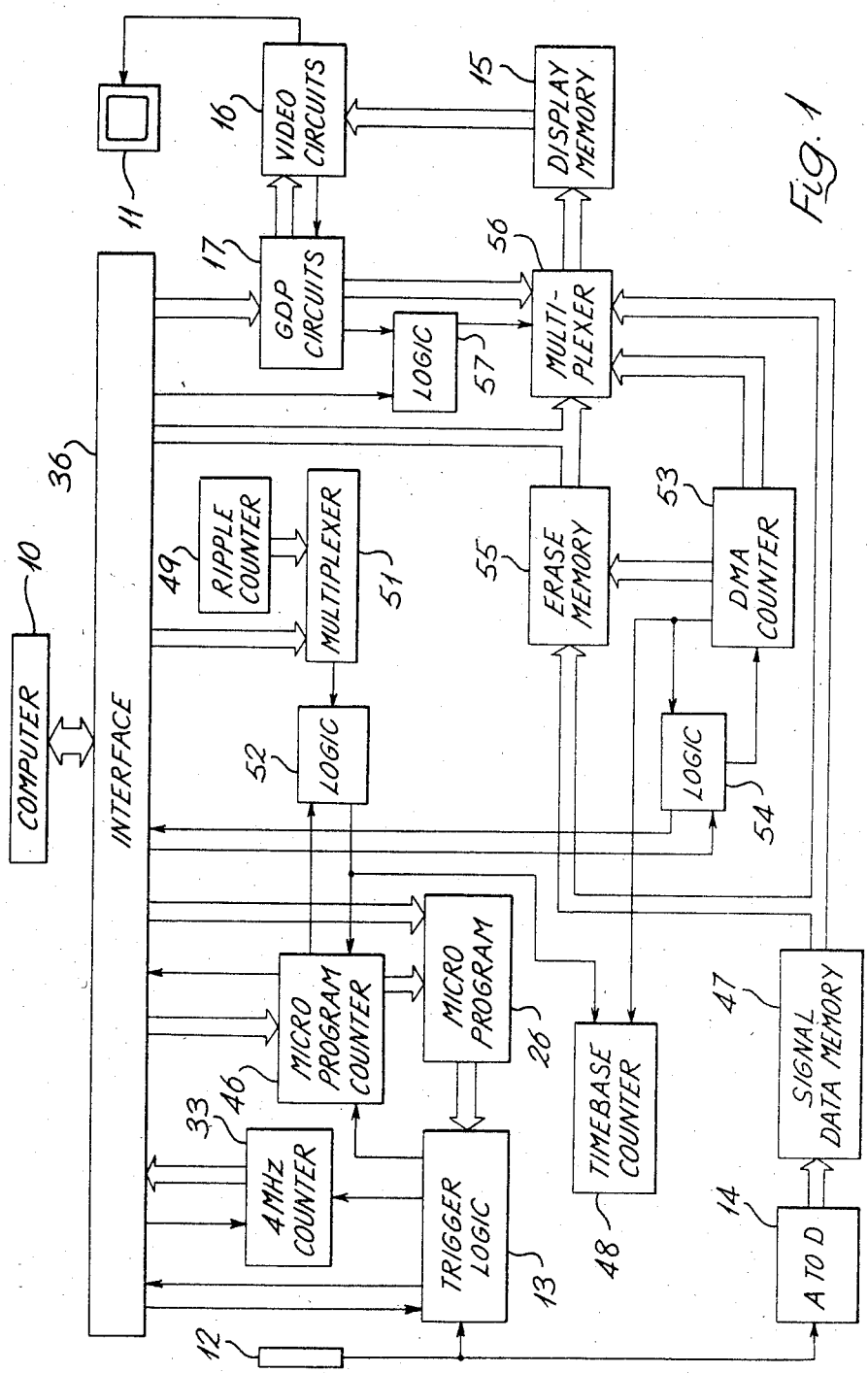
FIG. 1 is a block diagram of apparatus according to the invention.

The overall system will first be briefly described with reference to FIG. 1 where a computer 10 which may be a Z80 microprocessor controls a display 11 for displaying SFEMG waveforms from an electrode 12, trigger levels used in analysing such waveforms and various results of analysis carried out by the computer 10 relating to intervals between trigger signals. Signals from the electrode 12 are passed to a trigger logic circuit 13 which signals to the computer 10, for analysis, when certain trigger conditions have been fulfilled. Signals from the electrode 12 are also passed to an analogue-to-digital converter 14 and used in a way which is described in more detail below to provide an input for a display memory 15 which allows video circuits 16 to display the waveform. Graphic display circuits 17 allow the computer 10 to display alphanumerics and graphics and such display may be at the same time as the EMG waveform is displayed.

Figure 2:
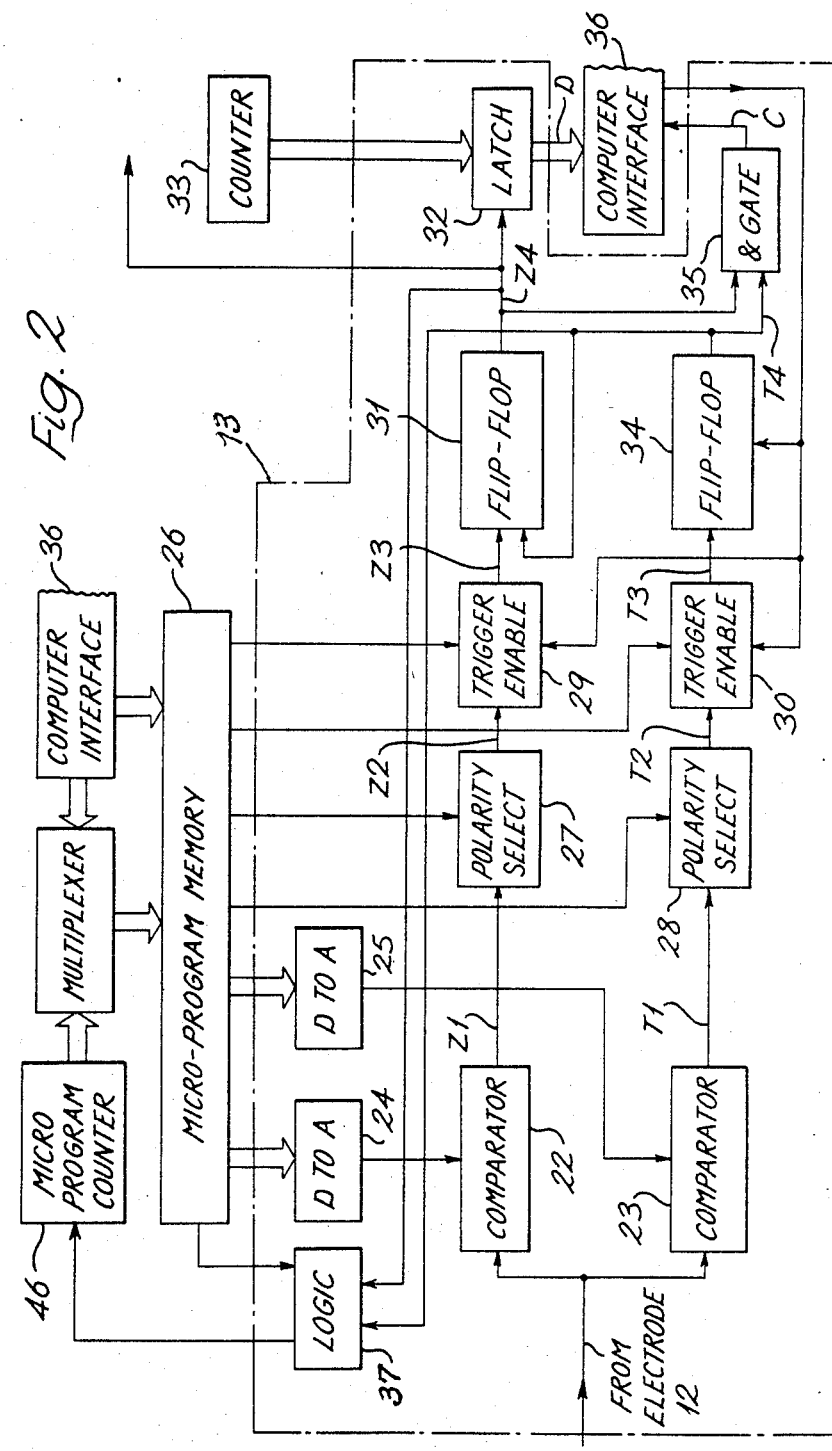
FIG. 2 is a block diagram of part of FIG. 1 showing the trigger logic in more detail.
Figure 3A:
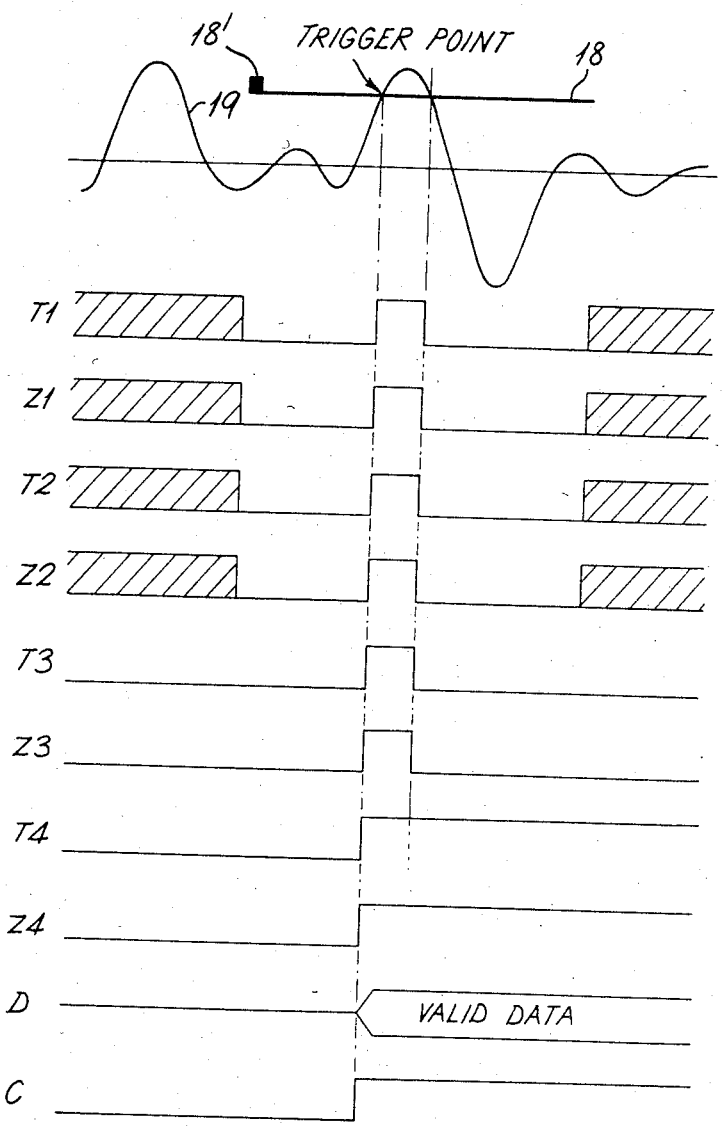
FIGS. 3a to 3c show waveforms used in explaining the operation of the trigger logic when set to provide three different types of trigger.
Figure 3B:
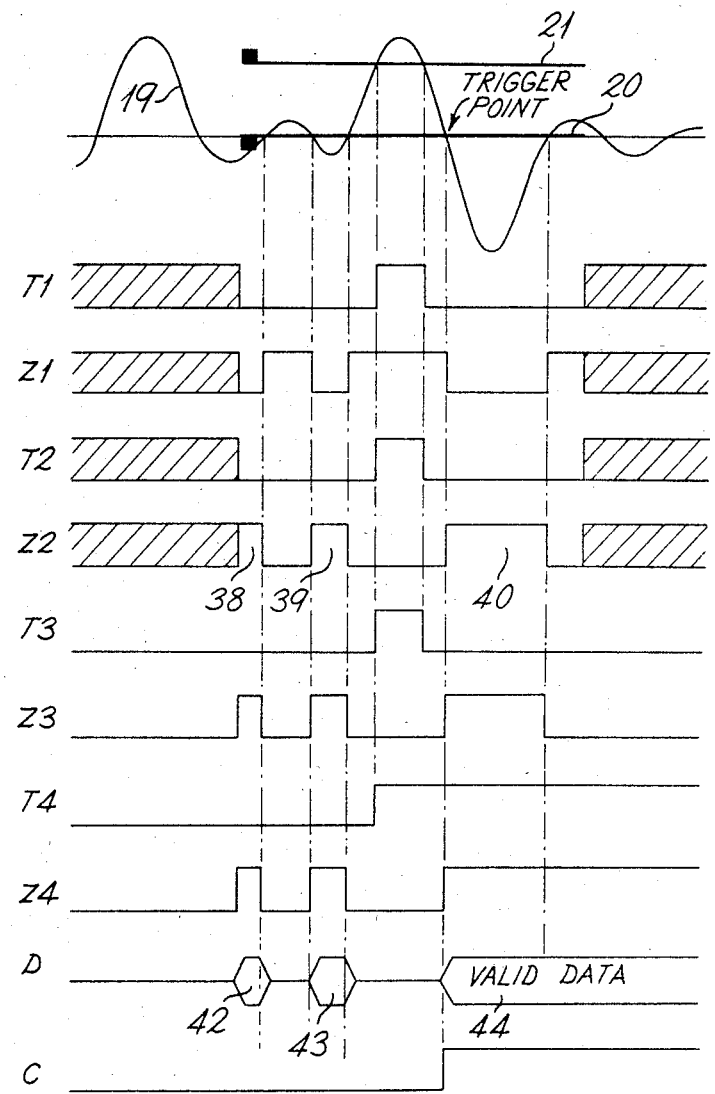
Figure 3C:
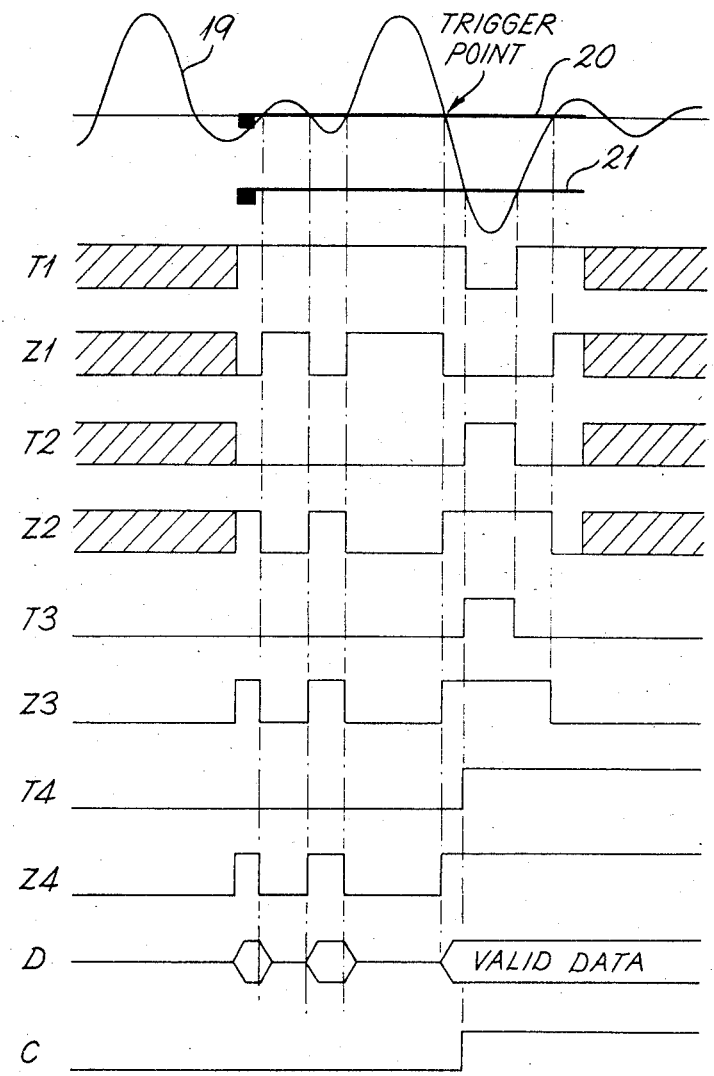

The trigger logic 13 is shown in more detail in FIG. 2 and allows three types of triggers shown in FIGS. 3a, 3b and 3c to be used. In these figures the waveforms shown are given the same designations as points at which the waveforms occur in FIG. 2.

A type 1 trigger provides an output causing a timing signal to be read into the computer 10 when an EMG waveform 19 (see FIG. 3a) exceeds an adjustable level 18. However the trigger can only be satisfied if the level 18 is exceeded during a "window" illustrated by the length of a line 18. A type 1 trigger may be set to occur when the waveform is going positive when it crosses the trigger level or when the waveform is negative going. The square 18' indicates that the trigger illustrated has been set to be satisfied by a positive going waveform while if the square 18' had been below the line 18 then the trigger would have been satisfied by a negative going waveform.

In FIGS. 3b and 3c the conventions regarding window length and direction of waveform to satisfy trigger level are the same as those of FIG. 3a.

Type 2 triggers (FIG. 3b) have two trigger levels: a zero trigger level 20 and a threshold trigger level 21. For a type 2 trigger timing data is read to the computer 10 when the zero trigger 20 is satisfied providing the threshold trigger 21 has previously been satisfied.

The type 3 trigger shown in FIG. 3c again uses the zero trigger 20 and the threshold trigger 21 but in this case timing data, valid when the threshold zero 20 is satisfied, is read into the computer provided the threshold trigger 21 is later satisfied before the zero trigger 20 is again satisfied.

Triggers 18, 20 and 21 are set by the computer 10 as will be described later and are adjustable in respect of level (positive or negative), window length and direction of EMG waveform to satisfy trigger.

In FIG. 2 signals from the electrode 12 are passed to comparators 22 and 23 which correspond to the zero trigger 20 and the threshold trigger 21, respectively. The levels of these triggers are set by the outputs of digital-to-analogue converters 24 and 25 which in turn are set by signals from a microprogram memory 26 controlled in a way which is described later. In some cases it is desirable to set the zero trigger 20 to a value which is not quite zero in order, for example, to overcome baseline instability. For type 1 triggers the inputs to both converters 24 and 25 are set to a digital value corresponding to the level of the trigger 18.

Signals from the comparators 22 and 23 are applied to polarity select circuits 27 and 28 which determine whether the triggers are to be satisfied by positive or negative going waveform portions. The circuits 27 and 28 carry out an exclusive OR function between output signals from the comparators and a signal supplied from the microprogram memory 26. The triggers are only active while the windows are active, enable circuits 29 and 30 providing this function again under the control of the memory 26.

Should a portion of a waveform satisfy the conditions implied by the three circuits 22, 27 and 29, a flip-flop circuit 31 is set but only remains set, once the output of the circuit 29 returns to "low", if a flip-flop circuit 34 has also been set. For this purpose the flip-flop circuit 31 receives an additional input from the flip-flop circuit 34. When the flip-flop circuit 31 is set, a latch 32 is held at the value at that instant of a 4MHZ counter 33 which continually cycles through its various states. If a flip-flop 34 has also been set, an AND gate 35 signals an interface 36 causing the computer 10 to read the contents of the latch 32. The flip-flop 34 is only set if the conditions implied by the circuits 23, 28 and 31 have been satisfied.

For a type 1 trigger the waveforms at the outputs of the comparators 22 and 23 are as shown as T1 and Z1 respectively, providing a positive going pulse when the EMG waveform 19 exceeds the trigger level. Since the trigger 18 is satisfied by a positive going waveform the outputs T2 and Z2 of the polarity select circuits 28 and 27 are also positive going pulses. The trigger enable circuits 29 and 30 set the duration of the window and the shaded areas of the waveforms T1, Z1, T2 and Z2 correspond to inhibition of the window and therefore indicate that it is irrelevant what value these waveforms have in the shaded areas. Since the window is enabled when the pulses of the waveforms Z2 and T2 occur the outputs of the enable circuits 29 and 30 (Z3 and T3) are pulses as shown. These pulses set the flip-flops 31 and 34 (outputs Z4 and T4) at the times shown so that time data in the form of the contents of the counter 33 are read into the latch 32, applied to the computer interface 36 by way of a channel D and accepted when the output C of the AND gate 35 indicates that both T4 and Z4 are "high". Thus valid data are passed to the computer 10.

In the example of a type 2 trigger shown in FIG. 3b the zero threshold comparator has the waveform Z1 but only the negative going portions 38, 39 and 40 pass the polarity select circuit 27 and provide positive going pulses at the output (Z3) of the trigger enable circuit 29. Thus the flip-flop 31 is set as shown at Z4 and data are applied to the computer interface as shown at 42, 43 and 44 by the latch 32. However the data are only accepted by the computer interface when the AND gate 35 provides a high output C. The threshold trigger 21 provides output pulses T1, T2 and T3 while the window is enabled, when it is exceeded by the positive going EMG waveform 19. Therefore the flip-flop 34 provides an output T4 at the time shown and the AND gate 35 is set when the flip-flop 31 goes positive as the waveform 19 passes through zero going negative. Thus unless the threshold trigger 21 has been satisfied, priming the flip-flop 34, a negative going zero crossing will not cause the computer interface to accept data from the latch 32. Hence in this example, only data present at 44 is passed to the computer.

A similar type of examination of FIG. 3c shows that data held by the latch 32 when the waveform 19 is negative are only accepted as valid data when the threshold trigger 21 is satisfied. Each time the waveform 19 crosses the zero threshold going negative the contents of the latch 32 are re-written from the counter 33 so it is only those zero crossings which are followed by a waveform portion satisfying the threshold 21 which result in valid data being read to the computer.

Having received the times at which certain trigger conditions are satisfied, as set by the computer 10 by way of microprogram memory 26, the computer is able to analyse the intervals between pulses.

The way in which the trigger logic is controlled by the microprogram memory 26 is now described.

The microprogram memory 26 is typically a 512 by 24 bit memory where the display 11 has a resolution of 512 by 512. Thus there is one 24 bit word for each x-coordinate of the display, these words storing control signals for the trigger logic 13. A microprogram counter 46 steps the memory 26 through its 512 positions but since it is also used as a sweep counter it is started at a value typically 100 when the trigger conditions are first satisfied. Thus the first 100 positions cannot be used. The reference values for the first trigger are programmed in the last positions of the microprogram.

Each 24 bit word held by the microprogram memory 26 has three fields:

(1) 8 bits to be passed to a selected one of the digital-to-analogue converters 24 and 25 to set the threshold levels, (2) 8 latched bits which remain as set until changed in which the first bit is for the purpose of restarting the time base as will be explained later and the fifth and sixth bits determine whether the threshold trigger and the zero trigger should act on positive or negative going waveforms. It is these bits which are applied to the polarity select circuits 28 and 27 respectively, and (3) 8 pulsed bits which must be present in each microprogram word where the corresponding function is to occur. The first and second bits control data transfer to the digital-to-analogue converters 24 and 25, respectively, so that when a one is present the bits held in the first field are read into the appropriate digital-to-analogue converter. The third and fourth bits enable the threshold and zero triggers respectively and hence are applied to the trigger circuits 30 and 29, while the fifth and sixth bits disable these trigger circuits.

The bits not mentioned above are available for further control functions which may be added as required.

The microprogram memory 26 is loaded from the computer 10 via the interface 36 in accordance with a program held by the computer and a user input to the computer. The computer program displays a menu which under one heading provides a further display requesting settings for the windows and trigger levels. The program then translates these requests into the 512 24 bit words for the memory 26.

As has been mentioned above, the microprogram memory starts to step through its stored words when the trigger conditions are first satisfied and thus the first trigger is different in operation from subsequent triggers in that windows and inter-potential time interval measurements are made with reference to the time when trigger conditions are first satisfied. Thus the first trigger has no windows and, in effect, synchronises the waveform display.

For a type 1 trigger, the microprogram sequence begins, therefore, when the threshold/zero level is crossed and for a type 2 trigger the sequence begins when the zero level is crossed following the threshold crossing.

For a type 3 trigger the microprogram sequence begins when the zero level is crossed but is terminated and restarted if this level is crossed again in the opposite direction if the threshold level has not been crossed. Thus the threshold level must not be reset for a subsequent trigger until the threshold level for the first trigger has been satisfied. For this purpose the first latched bit (referred to above and called the restart bit), is set aside to cause the microprogram to jump back to the beginning of the sequence (that is, in this example, corresponding to a microprogram counter value of 100). In the sequence of words the restart bit in one of the words prior to that word which readjusts the threshold level for the second trigger, is set to cause a logic circuit 37 (see FIG. 2) to reset the counter 46 to 100 unless the threshold level has been crossed.

In order to display that part of the SFEMG waveform which is of interest the output of the analogue-to-digital converter 14 is continually read into a data signal memory 47 under the control of a time base counter 48. Thus the memory 47 continually cycles through its 512 locations storing the digital version of the SFEMG waveform. The time base for the display is based on a ripple counter 49 which provides 8 selectable time base signals for time bases varying from 1.25 milliseconds to 160 milliseconds. Selection is by using a multiplexer 51 under the control of the computer 10 by way of the interface 36. Signals from the ripple counter 49 reach the time base counter 48 by way of a logic circuit 52 which disables the time base when the microprogram counter reaches 512. However since the microprogram counter 46 is initially set to 100, the data signal memory 47 then contains 100 values which precede satisfaction of the trigger conditions as well as 412 subsequent values and this allows a portion of the waveform prior to satisfaction to be displayed as well as a following portion.

When the microprogram counter 46 has reached 512 it signals the computer which passes a further signal to a direct memory access counter 53 by way of a logic circuit 54. The display memory 15 is updated either from the signal data memory 47 or from an erase memory 55 during line and frame flyback periods of the display 11. It is the function of the logic circuit 54 to enable the counter 53 on receiving a control signal from the interface 36 but to do so only during flyback periods.

Under the control of the counter 53 the signal data memory 47 is read into the display memory 15 by way of a multiplexer 56 and also into the erase memory 55. The display memory 15 contains three planes (red, blue and green) each of 32K by 8 bits. Thus there are three bits for each pixel giving a resolution of 512 by 512 in seven colours plus black. The erase memory 55 is provided to erase a waveform which has been entered into the display memory by transferring data from the erase memory to the display memory, with the colour set to black. Thus only the pixels which were previously set are reset during an erase cycle and this is considerably faster than resetting every bit of memory.

The GDP circuits 17 cause whatever is held in the display memory 15 to be displayed but the contents of this memory depend not only on data fed from the signal data memory 47 and the erase memory 55 but also from the GDP circuits 17. Data from the GDP circuits 17 relate to alphanumeric displays such as the menu mentioned above, lines 18, 20 and 21 of FIGS. 3a, 3b and 3c (preferably in different colours) and analysis outputs such as histograms. These displays are mentioned to give an overall picture of an SFEMG analysis apparatus but neither the GDP circuit 17 nor the analysis programs which may be carried out by the computer 10 form part of the present invention. The GDP circuit 17 may be as indicated in the Thomson-EFCIS data sheet for its graphic display processor integrated circuits EF 9365 and EF 9366, either of these processors being used as the basis of the circuits 17. The display memory 15 and the video circuit 16 may also be as indicated in this data sheet.

The GDP circuits 17 therefore display whatever is held by the display memory 15 and typically the signal data memory 47 and the erase memory 55 are used to load that part of the display memory which corresponds to the lower 256 by 512 pixels. The lower half of the screen then displays the waveform and the GDP circuits superimpose other information on the waveform, such as the axis, the trigger levels and windows, and if required a "trigger satisfied" indication at the point of triggering. The GDP circuits display other information, such as menus in the upper half of the screen, but upper and lower halves can be reversed or used for other purposes as determined by the computer software. Whatever is held by the display memory 15 is displayed and as soon as a new waveform has filled the signal data memory 47 and has been signalled as being of interest by the trigger logic 13, the current waveform is erased by transferring the contents of the erase memory 55 to the display memory 15 and then the new waveform is displayed by transferring the contents of the signal data memory 47 to the display memory 15.

The logic circuit 57 is used to control the multiplexer 56 when the computer requests a waveform transfer and when the GDP circuits signal a line or frame flyback period.

Figure 4:
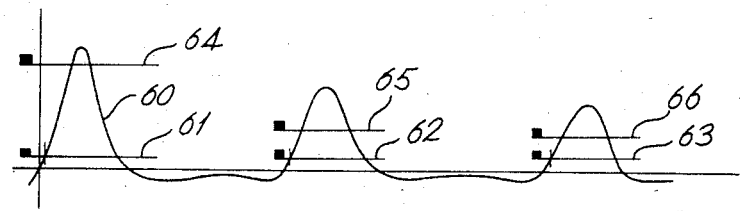
FIG. 4 illustrates part of a typical display produced by the apparatus of FIG. 1.

A typical SFEMG display is shown in FIG. 4 where the SFEMG waveform 60 passes through three peaks each of which are of interest in analysis of the waveform. If type 3 triggers are used then three zero triggers 61 to 63 may be set as shown and three threshold triggers 64 to 66 may also be set as shown. It will be appreciated that as the microprogram progresses, the trigger logic 13 is set as required to change from the triggers 61 and 64 firstly to the triggers 62 and 65 and secondly to the triggers 63 and 66. This is a versatile arrangement which saves considerably on the amount of hardware which would be required if each possible trigger were to have its own associated hardware.

The invention may be put into practice in many other ways than that specifically described and many variations may simply be made by reprogramming the computer 10 and the microprogram memory 26. For example the display may be organised at times so that two SFEMG waveforms are displayed one above the other for comparison. The microprogram counter may be set at other values than 100 in order to allow different portions of the SFEMG waveform to be displayed.

The first trigger may be set automatically as follows: When an operator selects an auto-trigger option, the computer sets the timebase to 160 msecs. and sets the reference levels to a large negative value providing a "free run" operation. When the signal data memory 47 is full the 512 amplitude samples are passed by way of the erase memory 55 to the computer where the optimum reference levels are calculated from mean and peak values. The timebase is next reset to its original value and subsequent waveforms are processed using the reference levels which have now been automatically set. Provision may be made to allow these levels to be adjusted manually.

Another automatic level setting option can be used during data acquisiton to overcome a problem of varying size of potential peaks due to slight movements of the single fibre needle electrode. The use of zero triggers allows threshold trigger levels to be altered to compensate for such varying peaks without affecting measured time relationships. In this option the computer reads each SFEMG waveforms and measures peak values during windows. The threshold trigger for each window is then set to a level, above the zero trigger, equal to five eighths of the peak value, a running average of peak values being used to ensure that there is no sudden change in level. The computer is also programmed to ignore the effect of the failure of an expected potential to appear by arranging for the level of the threshold trigger to remain the same if any peak has a value which is less than half the corresponding previous value.

By reading directly from the erase memory into the computer a hard copy of the waveform may be provided, for example by a dot matrix printer.

A second signal channel may be provided if the following circuits are added: an analogue-to-digital converter, a signal data memory, a multiplexer and a timebase counter, (these circuits being the same as, and performing similar functions to, circuits 14, 47, 51 and 48, respectively). The erase memory is also increased to store an extra 512×8 bits, the trigger logic 13 is modified to allow signals in either channel to be compared with the reference values and the microprogram is modified to control the second timebase.

Such an arrangement allows the second channel to be displayed with a different timebase setting from the first. If the second timebase counter is stopped by the microprogram at a predetermined time in relation to the first timebase counter, the second signal data memory contains the last 512 samples leading up to the predetermined time. Two displays can be provided controlled by the respective timebases, and if the second timebase has a shorter period than the first, the display it controls is a 'magnification' of a portion of the other display.

Displays corresponding to the two channels may be displayed in respective halves of the screen, or in the same half but with a d.c. offset for one display or in different colours.

Inter-channel measurements can be carried out; for example a stimulus may be displayed using one channel and a response using the other channel.

The first and second relationships may be tested in different channels such that a trigger is only satisfied if the signal in one channel satisfies one relationship and the signal in the other channel satisfies the other relationship. For example one channel may contain a differentiated version of an SFEMG signal and a trigger is only satisfied when both the amplitude and rate of change of the signal reach specified values.

We claim:

1. Apparatus for indicating when a waveform satisfies selected conditions, comprising:
   first and second comparator means for comparing the instantaneous value of the waveform with first and second reference values, respectively,
   means for adjusting the first and second reference values,
   means for generating a gating signal when the instantaneous value of the waveform has attained both a first predetermined relationship with the first reference value and a second predetermined relationship with the second reference value,
   clock means for providing an indication of time,
   latch means for holding the value of the clock means at the instant the first predetermined relationship is satisfied, and
   gate means for passing the contents of the latch means to output when the gating signal is generated.

2. Apparatus according to claim 1 wherein the means for generating a gating signal is so constructed that the first and second predetermined relationships are satisfied when the value of the waveform passes through the first and second reference values, respectively, in respective predetermined directions.

3. Apparatus according to claim 2 wherein the means for generating a gating signal includes means for selecting at least one of said predetermined directions.

4. Apparatus according to claim 1 including enabling means for at least one of the first and second comparator means for enabling said one comparator means during selectable time intervals.

5. Apparatus according to claim 4 wherein the means for adjusting the first and second reference values, the means for selecting at least one of said predetermined directions and the enabling means form at least part of a logic means, and the apparatus includes memory means for storing at least one of said reference values, relationships and selectable time intervals, and program counter means for controlling read-out from said memory means to the logic means, said program counter means being started when said gating signal is generated.

6. Apparatus according to claim 4 wherein the apparatus includes display means for displaying portions of the waveform applied to the apparatus and at least one of the following: one of the reference values and the duration of a selectable time interval for which one of the comparator means is enabled.

7. Apparatus according to claim 6 wherein the apparatus includes:
   signal-data memory means for storing signals representing waveform portions applied to the apparatus, the signal-data memory means having one storage location, capable of storing at least one digital signal for the x-coordinate of each of a plurality of picture elements in the display means, the display means displaying the waveform portions in dependence upon signals stored by the signal-data memory means, time base counter means for controlling the signal-data memory means to read signals continuously into its storage locations in a cyclic sequence, and program counter means for disabling the time base counter means each time a predetermined count is reached by the program counter means, the predetermined count being such that the signal-data memory means then holds signals corresponding to, and subsequent to, the generation of the gating signal which started the program counter means.

8. A method of providing an indication when a waveform satisfies selected conditions, comprising the steps of:

setting first and second reference values, comparing the instantaneous value of the waveform with the first and second reference values respectively, generating a gating signal when the instantaneous value of the waveform has attained both a first predetermined relationship with the first reference value and a second predetermined relationship with the second reference value, storing a value representing elapsed time at the instant the first predetermined relationship is satisfied, and passing the stored time value to output when the gating signal is generated.

9. A method according to claim 8 wherein the first reference value has a smaller magnitude than the second reference value, and the first and second relationships comprise passing through the first reference value in one direction and passing through the second reference value in the opposite direction, respectively.

10. A method according to claim 8, wherein the first reference value has a smaller magnitude than the second reference value, and the first and second relationships comprise passing through the first and second reference values, respectively, in the same direction.

* * * * *